(12) United States Patent
Park et al.

(10) Patent No.: US 10,628,659 B2
(45) Date of Patent: Apr. 21, 2020

(54) INTELLIGENT TUMOR TRACKING SYSTEM

(71) Applicant: INTERNATIONAL BUSINESS MACHINES CORPORATION, Armonk, NY (US)

(72) Inventors: Sun Young Park, San Diego, CA (US); Dustin Sargent, San Diego, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 73 days.

(21) Appl. No.: 15/822,893

(22) Filed: Nov. 27, 2017

(65) Prior Publication Data

US 2019/0163949 A1 May 30, 2019

(51) Int. Cl.
*G06K 9/00* (2006.01)
*A61B 5/00* (2006.01)
(Continued)

(52) U.S. Cl.
CPC .......... *G06K 9/0014* (2013.01); *A61B 5/7485* (2013.01); *G06K 9/4628* (2013.01); *G06K 9/6271* (2013.01); *G06N 3/0445* (2013.01); *G06K 2209/05* (2013.01); *G06T 7/0012* (2013.01); *G06T 7/11* (2017.01); *G06T 7/136* (2017.01); *G06T 2207/20081* (2013.01); *G06T 2207/20112* (2013.01); *G06T 2207/20212* (2013.01); *G06T 2207/30096* (2013.01)

(58) Field of Classification Search
CPC ........................................... G06T 2207/30096
See application file for complete search history.

(56) References Cited

U.S. PATENT DOCUMENTS 7,843,194 B2  11/2010  Kassai
8,204,290 B2   6/2012  Haras
(Continued)

OTHER PUBLICATIONS

Freitas, N. R., Vieira, P. M. & Lima, E. et al. (2017). Segmentation of bladder tumors in cystoscopy images using a MAP approach in different color spaces. Bioengineering (ENBENG). IEEE 5th Portuguese Meeting on. DOI: 10.1109/ENBENG.2017.7889429.
(Continued)

*Primary Examiner* — Oneal R Mistry
(74) *Attorney, Agent, or Firm* — Erik Huestis; Stephen Kenny; Foley Hoag LLP

(57) ABSTRACT

Evaluation of segmentation of medical imagery is provided. In various embodiments, a candidate segmentation of a medical image of an anatomical feature is received. The candidate segmentation is provided to a first trained classifier. An indication is received from the first trained classifier of the accuracy of the candidate segmentation based on one or more feature of the candidate segmentation. One or more prior segmentation of a prior medical image of the anatomical feature is received. The candidate segmentation and the one or more prior segmentation are provided to a second trained classifier. An indication is received from the second trained classifier of the accuracy of the candidate segmentation based on one or more feature of the one or more prior segmentation.

16 Claims, 13 Drawing Sheets

(51) Int. Cl.
  *G06N 3/04*    (2006.01)
  *G06K 9/62*    (2006.01)
  *G06K 9/46*    (2006.01)
  G06T 7/00      (2017.01)
  G06T 7/11      (2017.01)
  G06T 7/136     (2017.01)

(56) References Cited

U.S. PATENT DOCUMENTS

| | | | |
|---|---|---|---|
| 8,333,508 B2 | 12/2012 | Reiner | |
| 9,916,524 B2* | 3/2018 | Fanello | G06K 9/627 |
| 2008/0267468 A1* | 10/2008 | Geiger | A61B 8/13 |
| | | | 382/128 |
| 2009/0127451 A1 | 5/2009 | Watson et al. | |
| 2011/0075920 A1* | 3/2011 | Wu | G06K 9/4638 |
| | | | 382/160 |
| 2014/0200433 A1* | 7/2014 | Choi | A61B 5/4887 |
| | | | 600/407 |
| 2015/0359601 A1* | 12/2015 | Sauer | G06T 7/0012 |
| | | | 382/128 |
| 2016/0073992 A1 | 3/2016 | Liu | |
| 2016/0364878 A1* | 12/2016 | Guo | G06K 9/6202 |
| 2017/0056057 A1 | 3/2017 | Thapliyal et al. | |
| 2019/0030371 A1* | 1/2019 | Han | A61N 5/1039 |

OTHER PUBLICATIONS

Manoj, M. & Suresh, L. P. (2016). An Automated Multimodal Spectral Cluster Based Segmentation for Tumor and Lesion Detection in PET Images. International Conference on Circuit, Power and Computing Technologies (ICCPCT). DOI: 10.1109/ICCPCT.2016.7530326.

\* cited by examiner

2

INTELLIGENT TUMOR TRACKING SYSTEM

BACKGROUND

Embodiments of the present disclosure relate to imaging methods and/or systems, and more specifically, to imaging methods and/or systems that can compensate for image acquisition and algorithm variations.

BRIEF SUMMARY

According to embodiments of the present disclosure, methods of and computer program products for evaluation of segmentation of medical imagery are provided. In various embodiments, a candidate segmentation of a medical image of an anatomical feature is received. The candidate segmentation is provided to a first trained classifier. An indication is received from the first trained classifier of the accuracy of the candidate segmentation based on one or more feature of the candidate segmentation. One or more prior segmentation of a prior medical image of the anatomical feature is received. The candidate segmentation and the one or more prior segmentation are provided to a second trained classifier. An indication is received from the second trained classifier of the accuracy of the candidate segmentation based on one or more feature of the one or more prior segmentation.

DETAILED DESCRIPTION

Traditional medical imaging, such as those for tumor growth and treatment response assessment, have difficulty tracking the complexity of the tumor or lesion boundary and intensity patterns, resulting in inconsistent measurements of the same tumor or lesion among exams. In addition, lesion boundaries found by different automatic segmentation software can result in erroneous measurements. These differences are difficult for users to catch. Thus, there remains a need for an intelligent imaging tracking method or system to automatically segment and measure irregular and/or ill-defined imaging objects.

To address these and other shortcomings of alternative approaches, embodiments of the present disclosure relate to imaging tracking devices and/or systems, and more specifically, to imaging tracking devices and/or systems that can automatically segment and measure irregular and/or ill-defined objects in the image. In one aspect, the present disclosure provides an intelligent tumor segmentation guidance system. In some embodiments, the disclosed system can be used independently. In other embodiments, the disclosed system can be used in conjunction with a picture archiving and communication system (PACS). In particular embodiments, the disclosed system analyzes tumor segmentation results measured in different occasions and modalities. For example, the present disclosure can analyze segmentation associated with CT, MR, US, XA exams or other methods, and automatically finds potential segmentation errors. In some embodiments, the disclosed system can automatically correct the identified or suspected errors and/or request the user's feedback to correct the suspected errors.

A Picture Archiving and Communication System (PACS) is a medical imaging system that provides storage and access to images from multiple modalities. In many heathcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

Figure 1A:
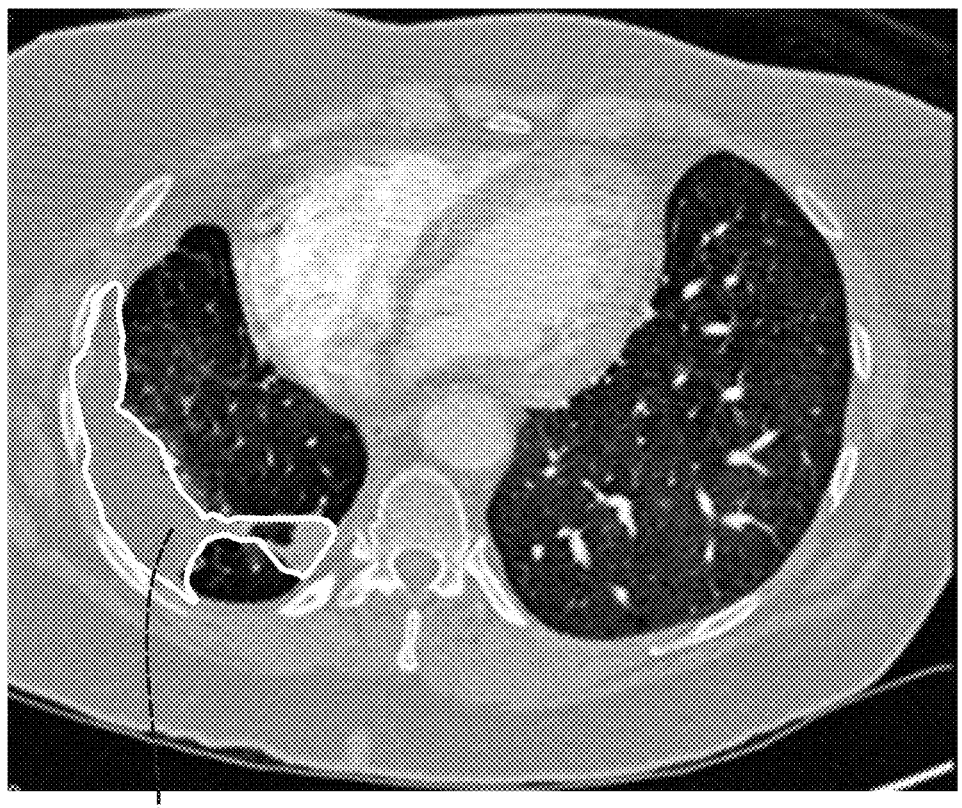
FIGS. 1A-B depict an exemplary imaging of irregular lesions in a lung nodule (FIG. 1A) or a brain edema (FIG. 1B) with an indeterminate boundary, showing different manual annotations by different users.
Figure 1B:
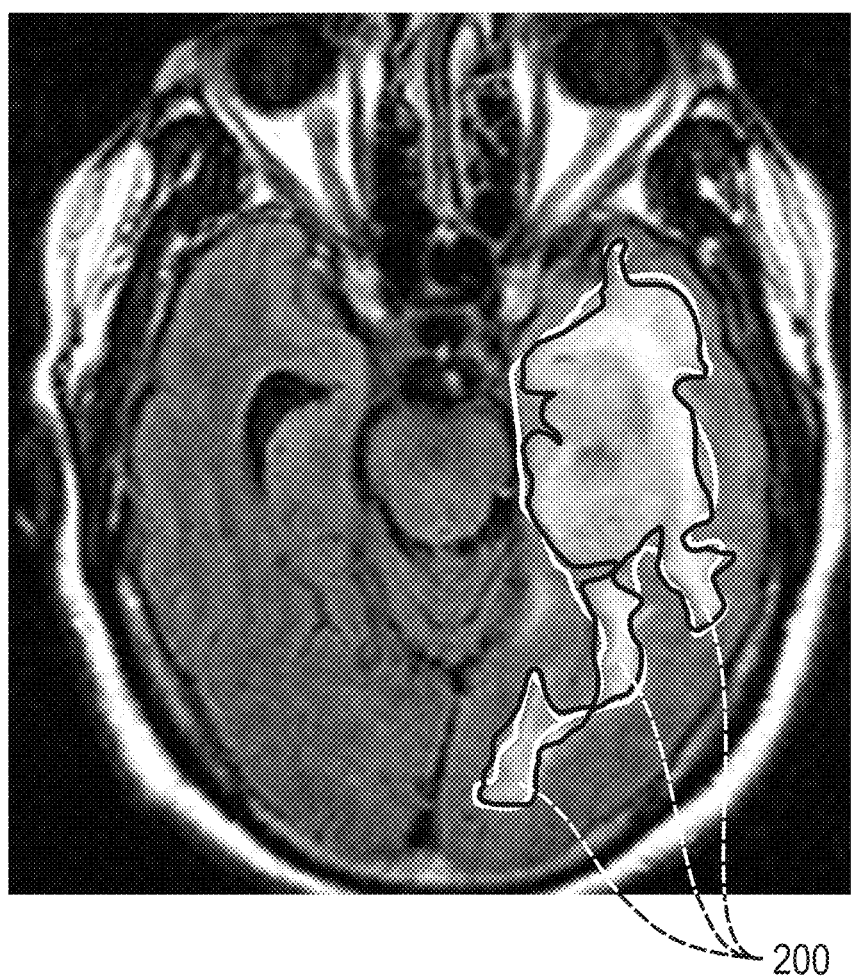

With reference now to FIG. 1, FIG. 1A shows an example of a lung nodule with an indeterminate boundary. The lesion is attached to other tissue, and there is no intensity discrimination between the lung nodule and other tissues. The contour, denoted by reference numeral 10, was manually added by a user. FIG. 1B shows an example of a brain edema. The lesion is separated into multiple components, denoted by reference numeral 20, and the intensity of the edema is not homogeneous. The contours of 100 and 200 of FIG. 1A and FIG. 1B were annotated by different users, thus exposing the contours to inconsistency. Indeed, studies have shown that manual tumor boundary annotations performed by different users can differ by up to 35%. Such inconsistency is problematic as it can lead to different measurement, diagnosis, and assessment for the same tissue sample.

Figure 2:
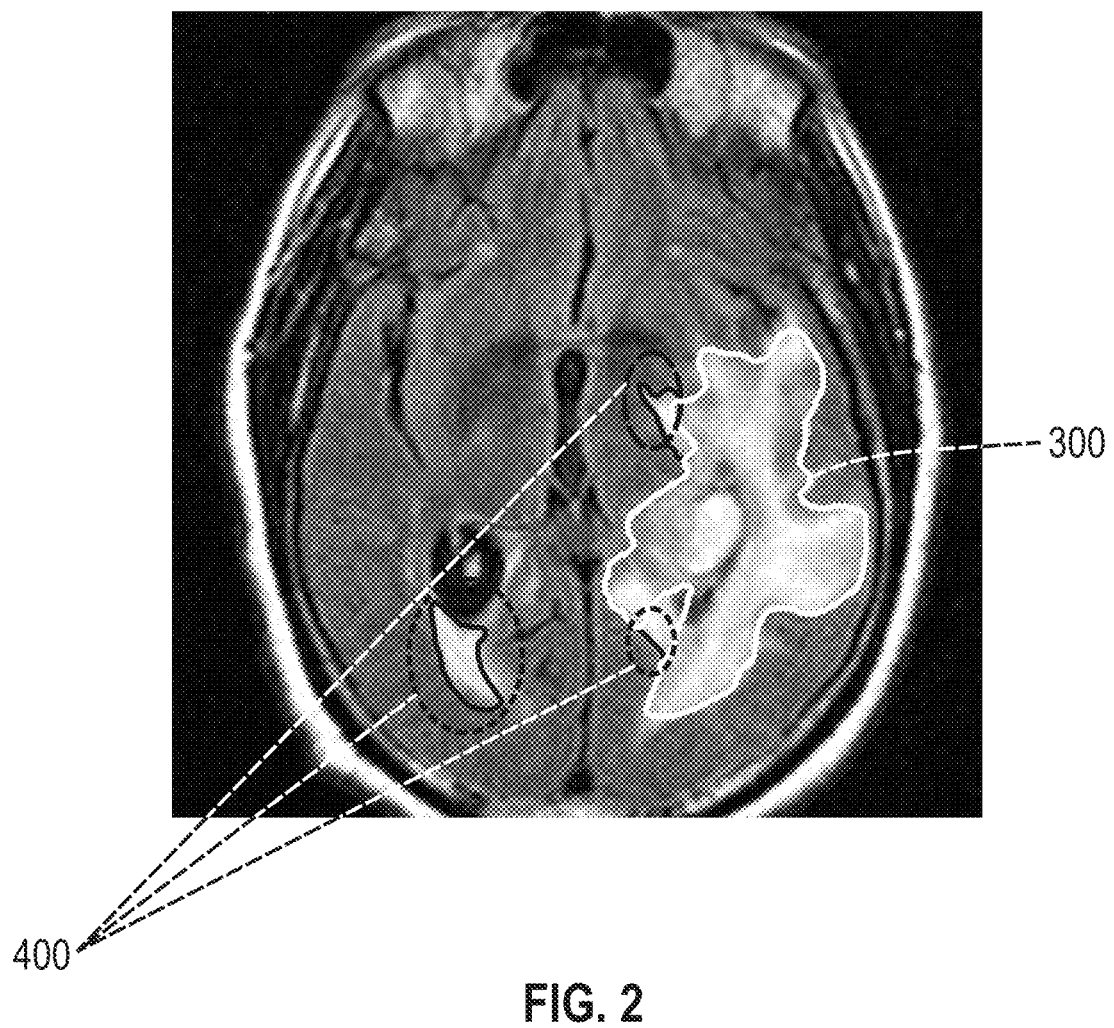
FIG. 2 depicts an exemplary imaging with a traditional automated segmentation algorithm, showing the difference between the automatic tumor segmentation result and a manually corrected result.

With reference now to FIG. 2, an exemplary automatic tumor segmentation result is shown as the contour denoted by reference numeral 300, and a manually corrected result is shown by reference numeral 400. In this exemplary view, a user added the contour 400 to correct the errors generated using an automated segmentation algorithm. Particularly, the circled regions highlight the discrepancy between the automated 300 and manual 400 of the segmentation.

Figure 3:
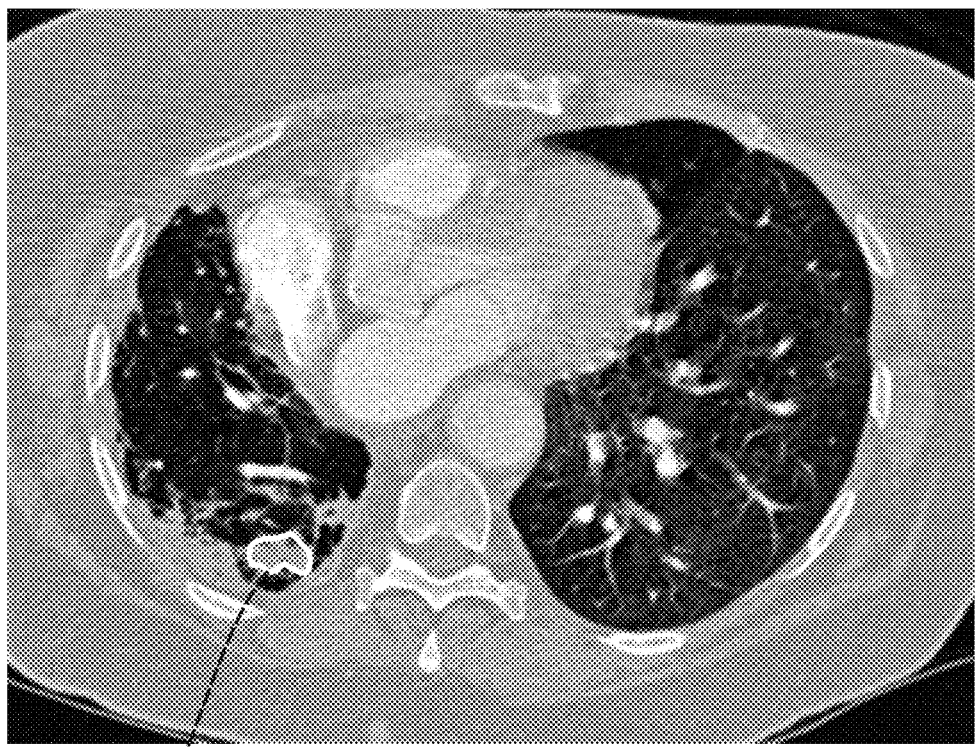
FIG. 3 depicts an exemplary lung nodule segmentation result automatically generated by a traditional algorithm, showing the failure to correctly track the nodule spreading surrounding areas.

With reference now to FIG. 3, an exemplary automatic lung nodule segmentation result is shown. The automatic contour 300 misses the surrounding areas in which the nodule has spread and attached to adjacent organs. Again, the inaccuracy of the automated contour is problematic as it can lead to ineffective or incomplete diagnosis and treatment.

It is common for traditional automatic segmentation algorithms to fail in correctly identifying or tracking the exact boundary of tumors, depending on the type of lesions and quality of images. Even though an automatic segmentation algorithm could reduce the manual labor required of the physician for manual measurement and contouring, the output still requires a clinician's validation to reduce errors that increase patient risk.

Embodiments of the present disclosure relate to a system that can estimate the quality of segmentation results and guide a user to correct the segmentation and provide more accurate measurements.

Figure 4:
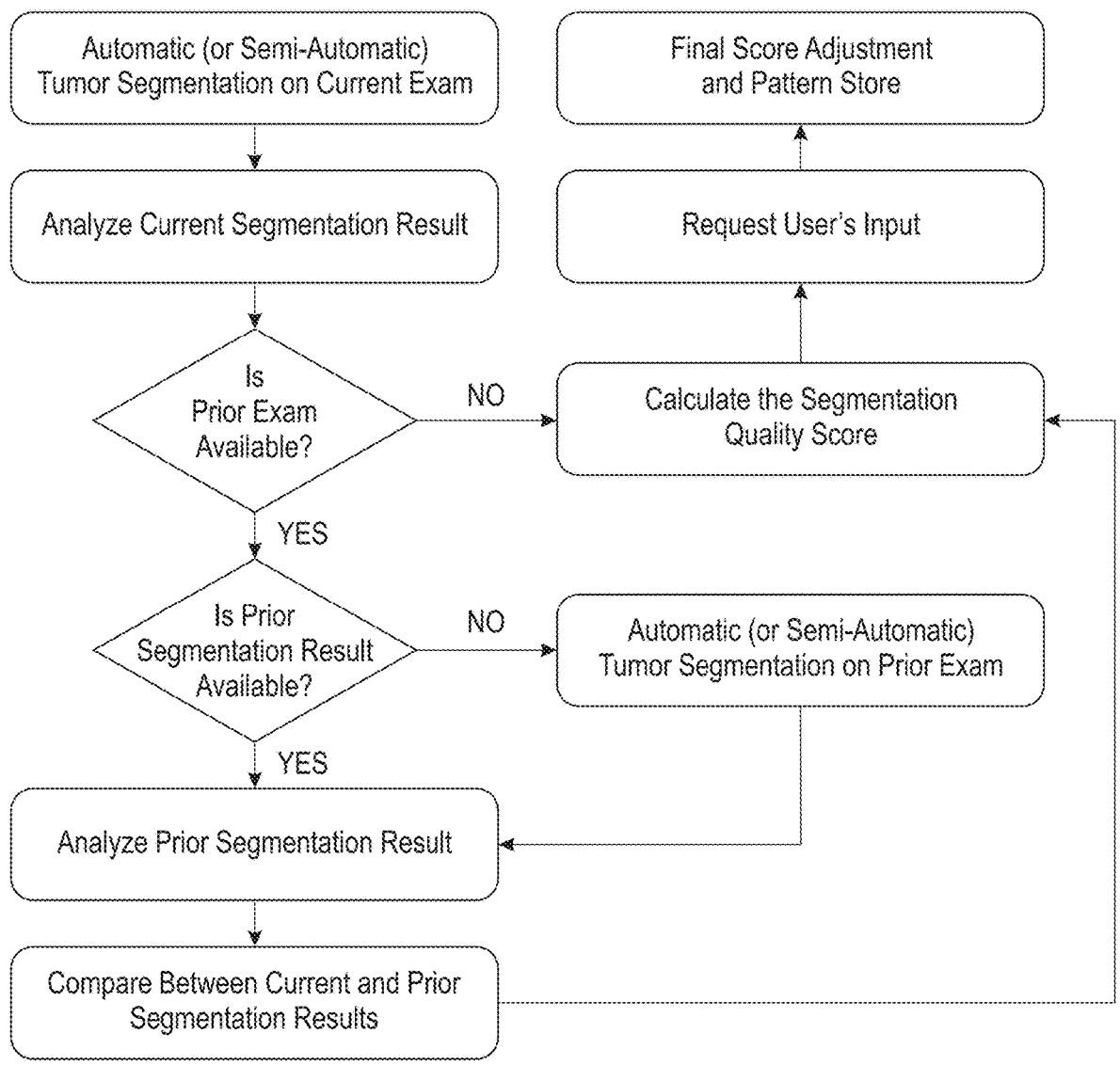
FIG. 4 depicts a workflow of an exemplary automatic tracking system according to an embodiment of the present disclosure.

With reference now to FIG. 4, a workflow chat of an exemplary system described herein is shown. The workflow begins with automatic or semi-automatic segmentation performed on a lesion in the current exam. Quality analysis is performed on the current segmentation. This could include many forms of analysis, such as comparing the boundaries with nearby edges, analyzing the smoothness/continuity of the boundary, etc. In some embodiments, an optional learning approach can also be applied to compare the current results with prior exams. For example, segmentation results can be fed to a neural network which can classify them as likely correct or incorrect.

Figure 5:
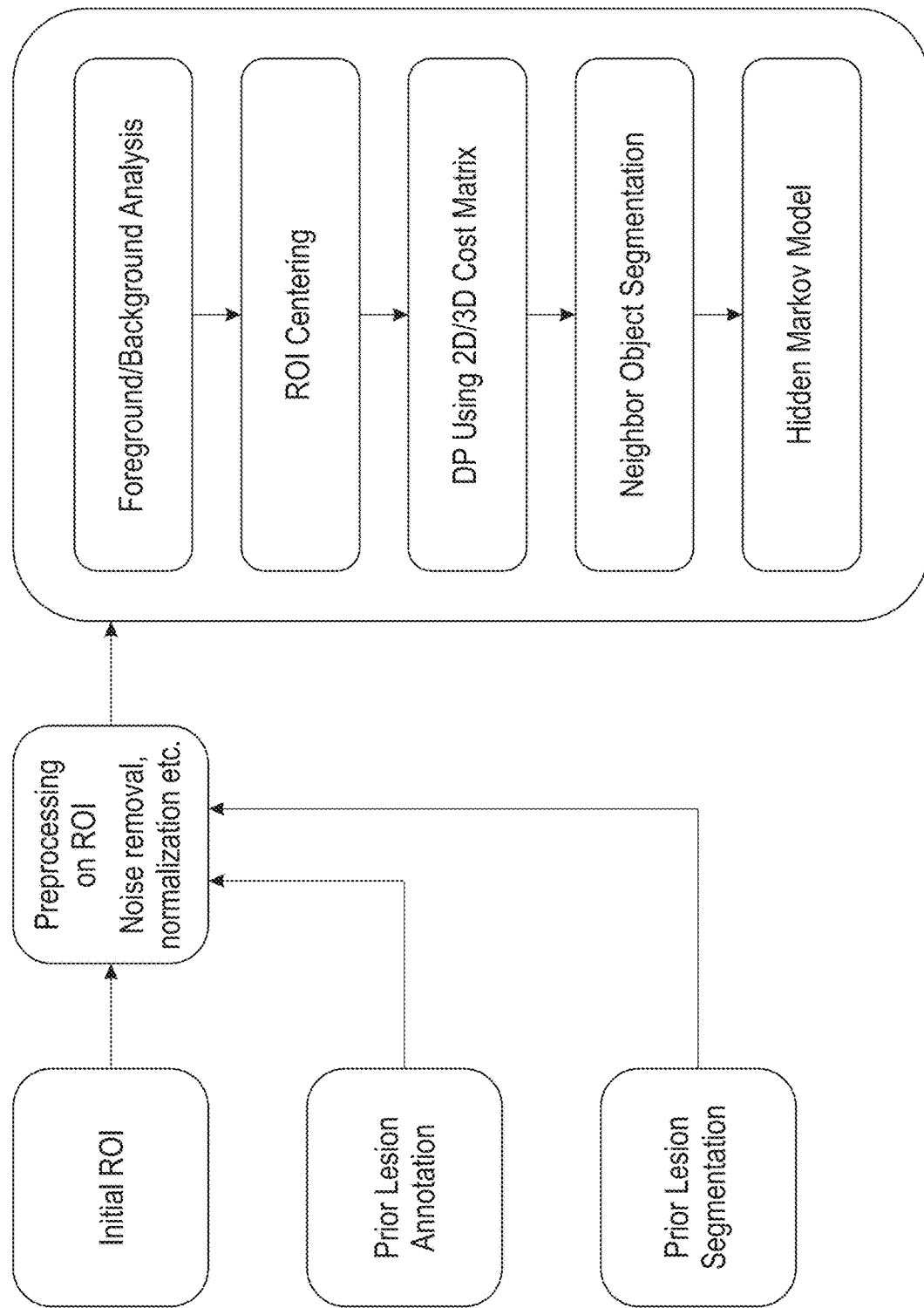
FIG. 5 depicts an exemplary semi-automatic segmentation algorithm used by an exemplary automatic tracking system according to an embodiment of the present disclosure.

With reference now to FIG. 5, a diagram of an exemplary module or algorithm for an automatic (or semi-automatic) segmentation process in an exemplary system described herein is shown. In this exemplary embodiment, the algorithm determines an initial region of interest containing the lesion based on a 2D input from a user and analysis of prior lesion annotation and segmentation results, if available. In some instances some initial processing of the prior results can be performed, e.g., noise removal, normalization, etc. Foreground/background separation is performed on the region of interest (ROI), which is then re-centered on the expected center of the lesion. A cost matrix is calculated from the ROI, and an initial lesion surface is determined using dynamic programming on the cost matrix. The results are then post-processed by removing neighboring attached objects like vessels, and ensuring proper 3D propagation from the initial 2D input slice, e.g., by using a Hidden Markov Model.

Figure 6:
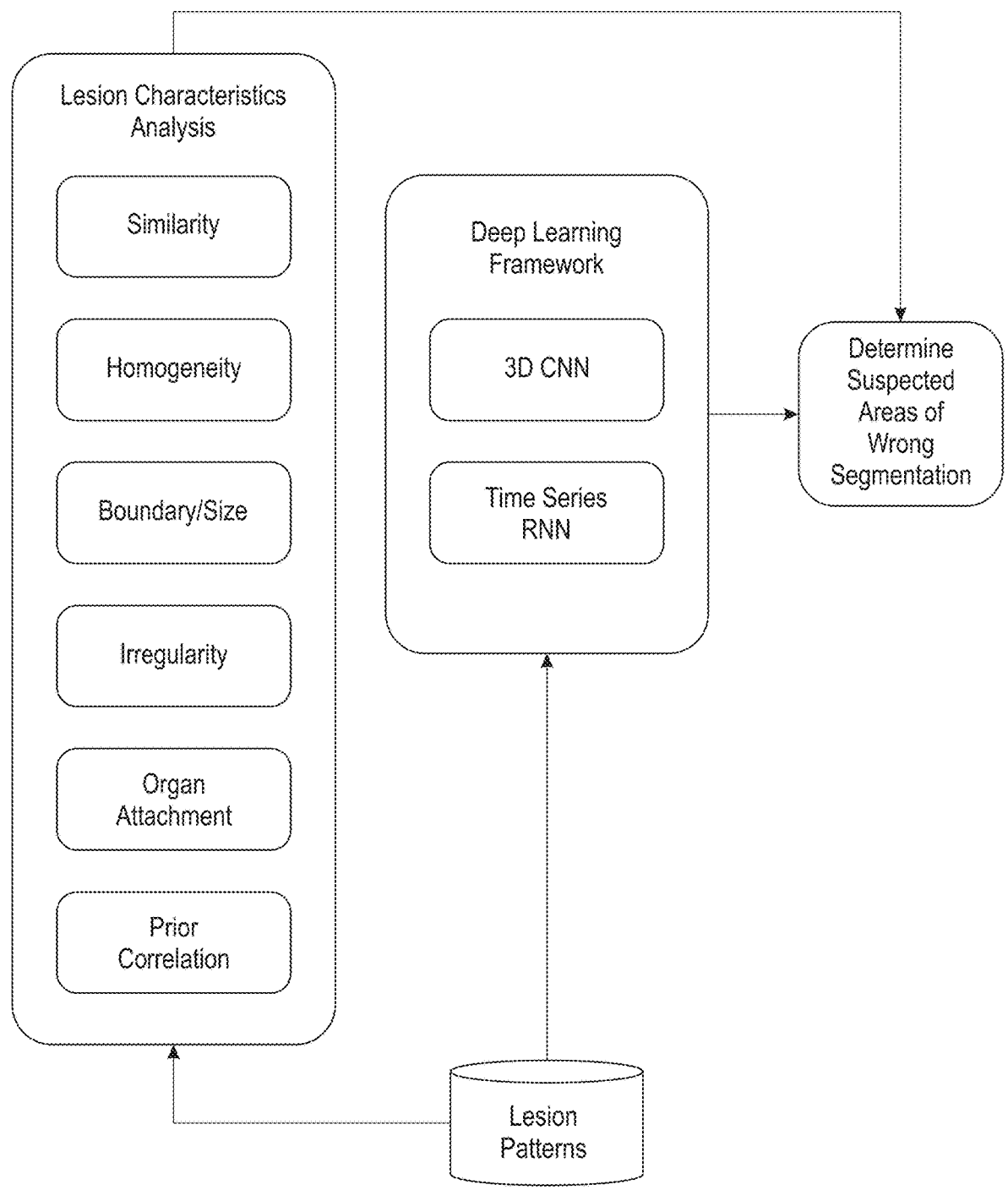
FIG. 6 depicts an exemplary module or algorithm, capable of analyzing segmentation quality, of an exemplary automatic tracking system according to an embodiment of the present disclosure.

With reference now to FIG. 6, a diagram of an exemplary module or algorithm for analyzing segmentation quality in an exemplary system described herein is shown. Multiple parameters can be analyzed as lesion characteristics and used to determine suspected areas of potentially wrong segmentation. Deep learning framework, generated from multiple lesion patterns collected through time, can be used to facilitate the determination of wrong segmentation.

In some embodiments, a feature vector is provided to a learning system. Based on the input features, the learning system generates one or more outputs. In some embodiments, the output of the learning system is a feature vector.

In some embodiments, the learning system comprises a SVM. In other embodiments, the learning system comprises an artificial neural network. In some embodiments, the learning system is pre-trained using training data. In some embodiments training data is retrospective data. In some embodiments, the retrospective data is stored in a data store. In some embodiments, the learning system may be additionally trained through manual curation of previously generated outputs.

In some embodiments, the learning system, is a trained classifier. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

Figure 7:
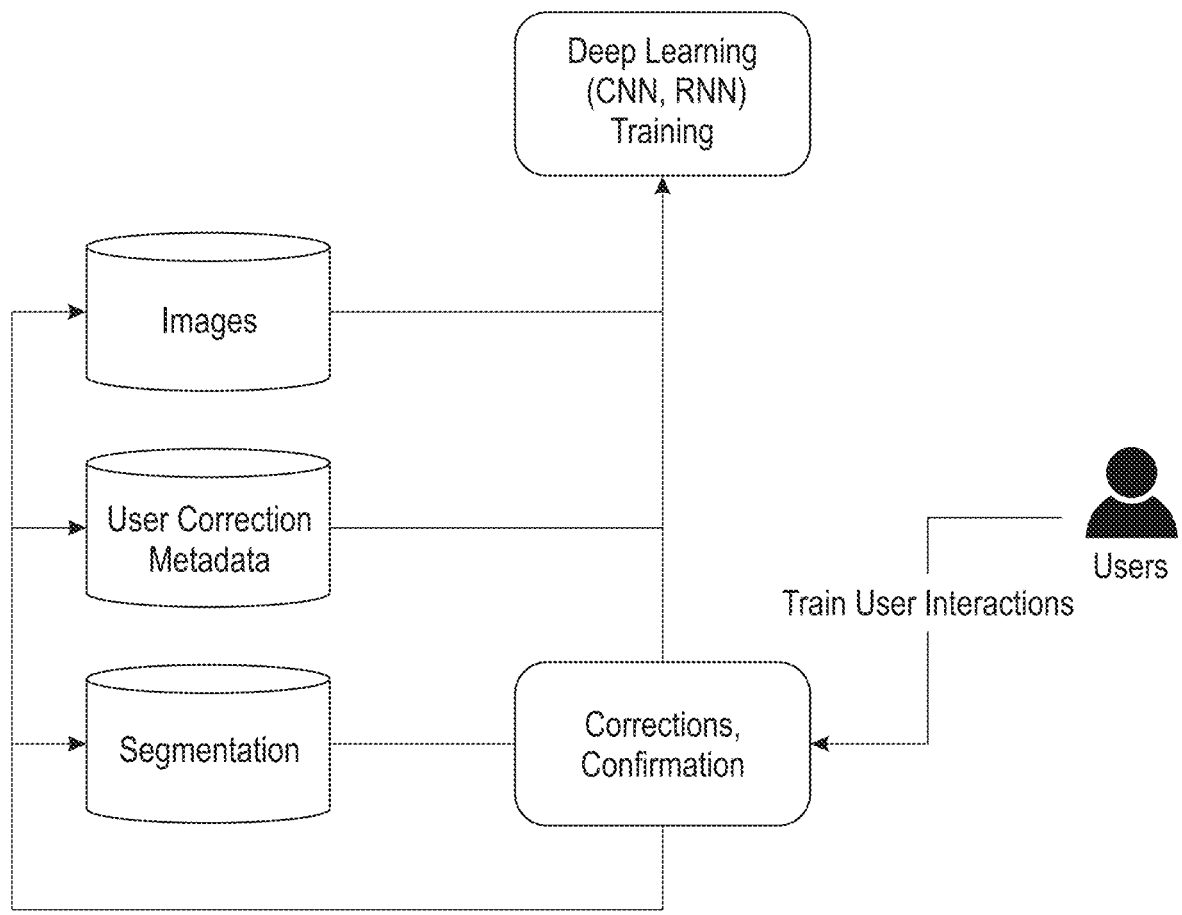
FIG. 7 depicts an exemplary module or algorithm, capable of learning and storing user patterns, of an exemplary automatic tracking system according to an embodiment of the present disclosure.

With reference now to FIG. 7, a diagram of an exemplary segmentation analysis block, such as a module or algorithm for learning and storing user patterns, is shown. This exemplary segmentation analysis block can be incorporated into the analyze segmentation result block shown in previous figures herein. For example, if prior segmentation results on the same lesion are available, they are also analyzed and compared with the current results. In some embodiments, this can be done with, e.g., a recurrent neural network (RNN) for time-series analysis to compare the prior and current candidate segmentation. From this analysis, a segmentation score can be generated along with areas containing potential segmentation errors. In some embodiments, the user's input is requested to manually correct the errors, followed by a final adjustment and output.

Figure 8:
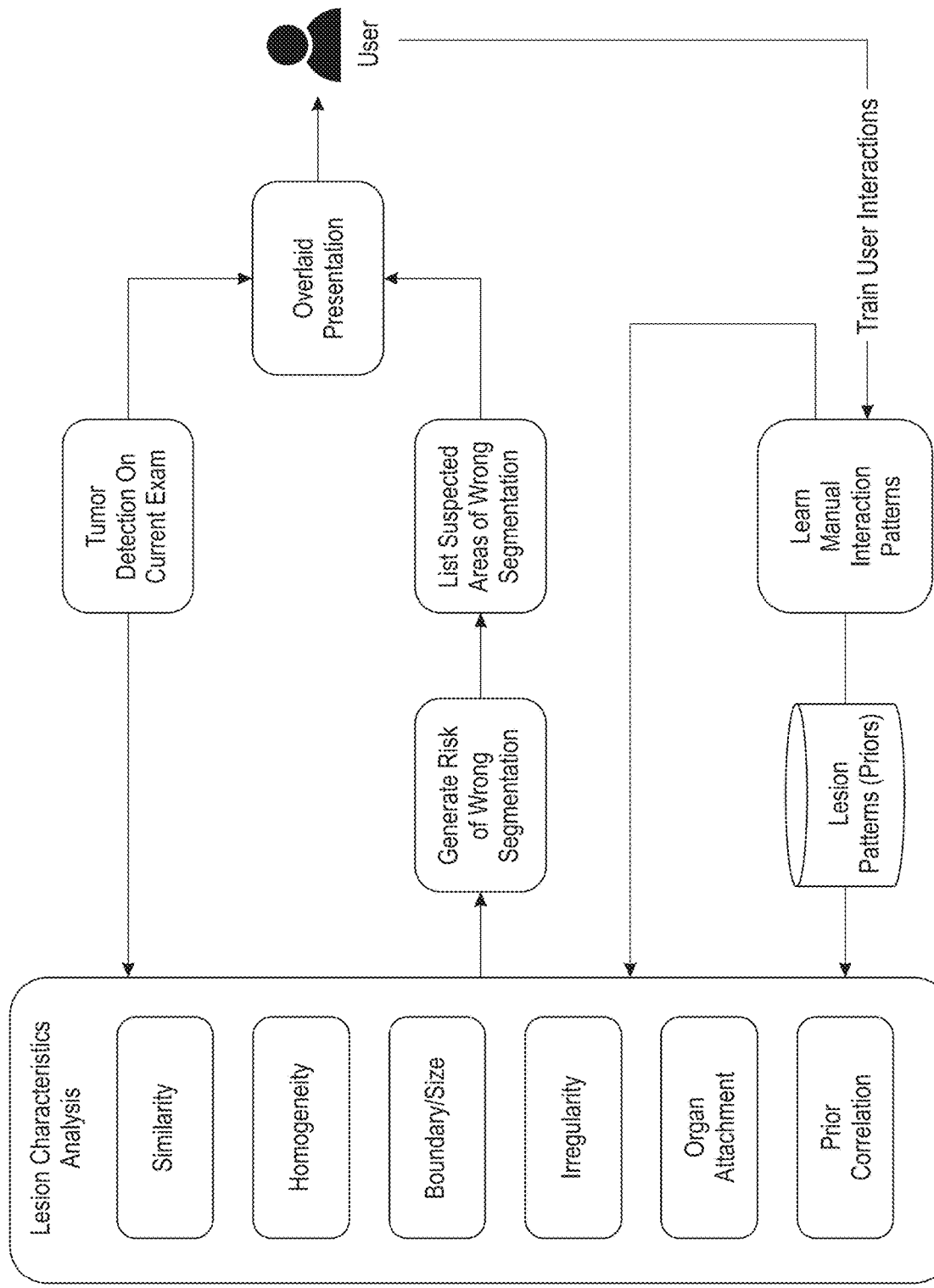
FIG. 8 depicts an exemplary modified module or algorithm, capable of analyzing segmentation quality modified by learned and stored user patterns, of an exemplary automatic tracking system according to an embodiment of the present disclosure.

With reference now to FIG. 8, a diagram of an exemplary modified segmentation analysis block, combined with an exemplary function of learning and storing user patterns, is shown. In this example, a user's input to correct previous segmentation is stored, compiled, and/or used to train the system to better correlate the tracking function and/or reduce segmentation errors.

Figure 9:
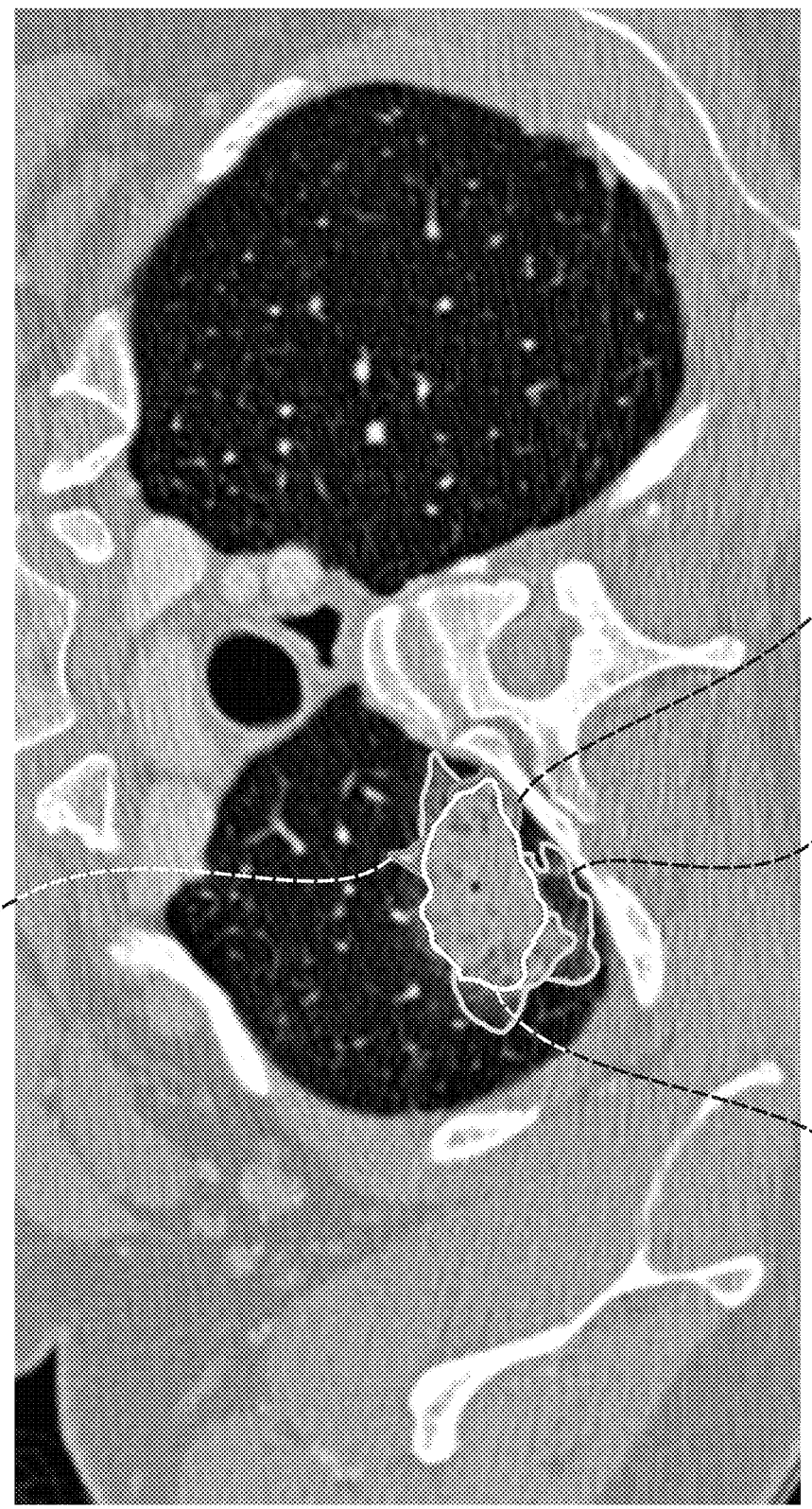
FIG. 9 depicts an exemplary automatic tracking system, capable of presenting score-based guidance for user selection, according to an embodiment of the present disclosure.

With reference now to FIG. 9, a diagram of an exemplary imaging display to the user, of the system described herein, is shown. The system offers score-based guidance in which areas in the image are identified and assigned scores for possible segmentation errors. For example, the "Certainty 1" outline indicates a region which is 100% certain to contain the lesion, the "Certainty 2" and "Certainty 3" outlines are 80% and 70%, respectively, likely to contain the lesion, and the "Certainty 4" outline is a region of 50% certainty. A user then can choose a region for segmentation analysis with an understanding of the possibility of error for choosing such area. Potential user corrections and/or feedback can be entered and stored for further learning and perfecting score assignment and, thus, the tracking system.

Figure 10:
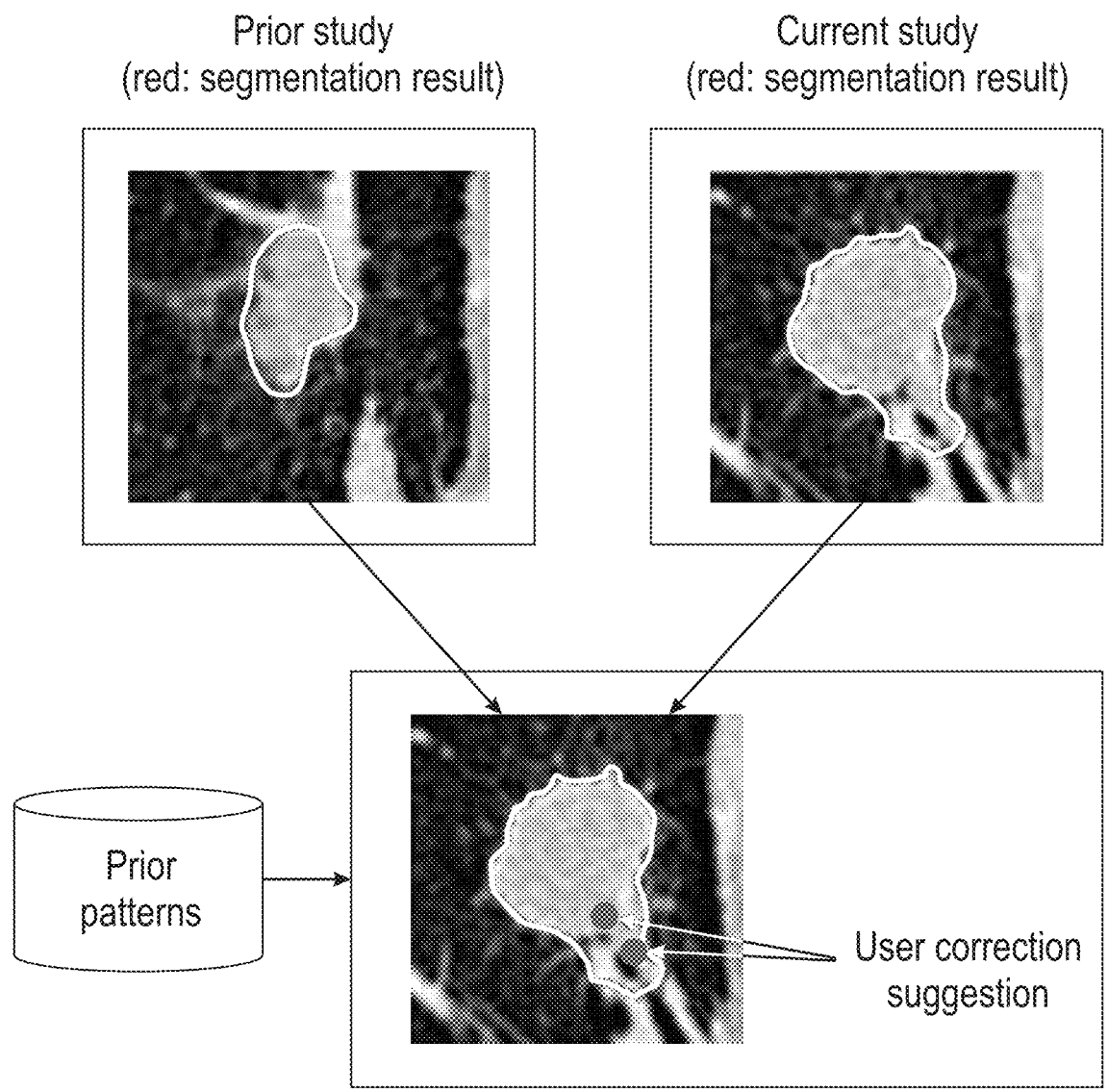
FIG. 10 depicts an exemplary automatic tracking system, capable of presenting indication marks for user correction and/or feedback, according to an embodiment of the present disclosure.

With reference now to FIG. 10, a diagram of an exemplary system described herein is shown. Such system is capable of presenting indication marks on objects tracked in the image to invite user correction or confirmation, which can be used for further learning and optimization of the tracking system. In FIG. 10, differences found between the prior and current lesions in images, as well as surrounding tissue identified as vessels, are marked as potential regions for the user to correct the segmentation. The user's feedback can be used to modify and optimize prior patterns and improve the tracking system.

One embodiment of the present disclosure comprises an imaging tracking system that can automatically segment and measure imaging objects, particularly, those objects with irregular boundaries, such as ill-defined lesions. Other embodiment of the present disclosure comprise an imaging tracking system comprising or in connection to a computing node performing at least one of phases and/or such tracking functions (e.g., automatic segmentation, analysis, adopting manual corrections, and/or learning and optimizing the tracking system or algorithm using prior pattern with or without manual correction/feedback). Such computing node, or any parts thereof, is only one example of a suitable computing node and is not intended to suggest any limitation as to the scope of use or functionality of embodiments of the disclosure described herein. Regardless, the computing node described herein is capable of being implemented and/or performing any of the functionality set forth hereinabove.

Figure 11:
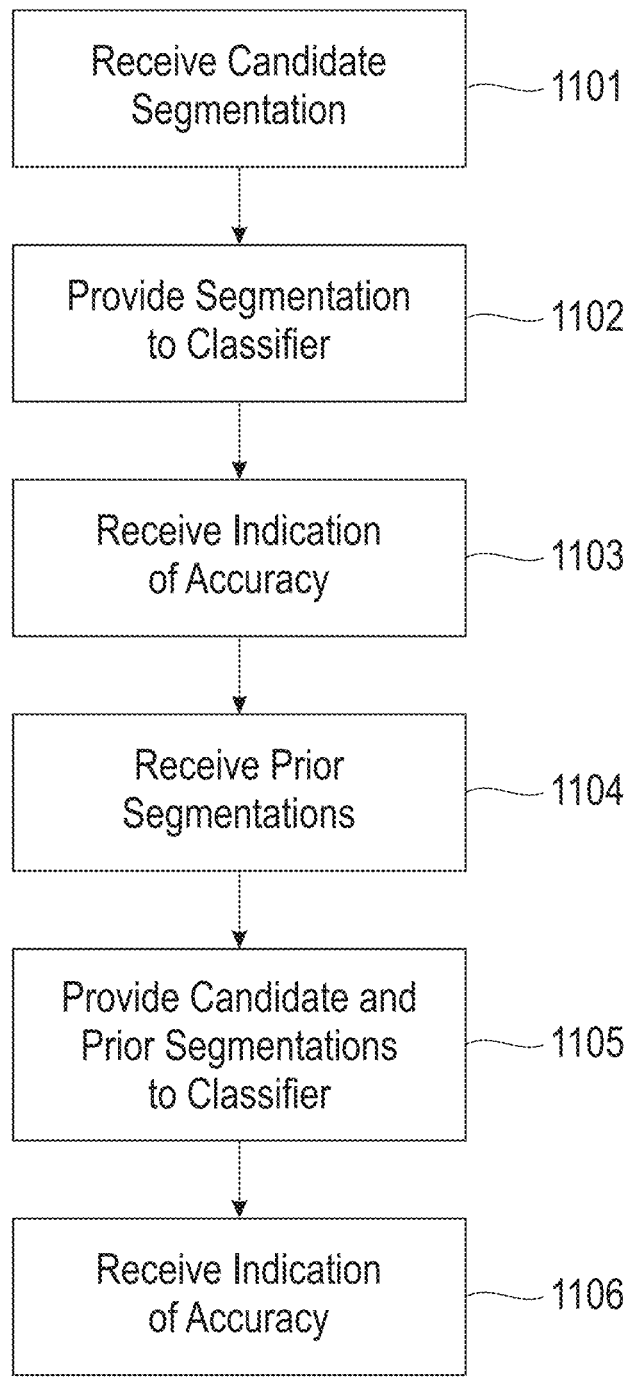
FIG. 11 illustrates a method for evaluation of segmentation of medical imagery according to embodiments of the present disclosure.

Referring now to FIG. 11, a method for evaluation of segmentation of medical imagery is illustrated according to embodiments of the present disclosure. At 1101, a candidate segmentation of a medical image of an anatomical feature is received. At 1102, the candidate segmentation is provided to a first trained classifier. At 1103, an indication is received from the first trained classifier of the accuracy of the candidate segmentation based on one or more feature of the candidate segmentation. At 1104, one or more prior segmentation of a prior medical image of the anatomical feature is received. At 1105, the candidate segmentation and the one or more prior segmentation are provided to a second trained classifier. At 1106, an indication is received from the second trained classifier of the accuracy of the candidate segmentation based on one or more feature of the one or more prior segmentation.

Figure 12:
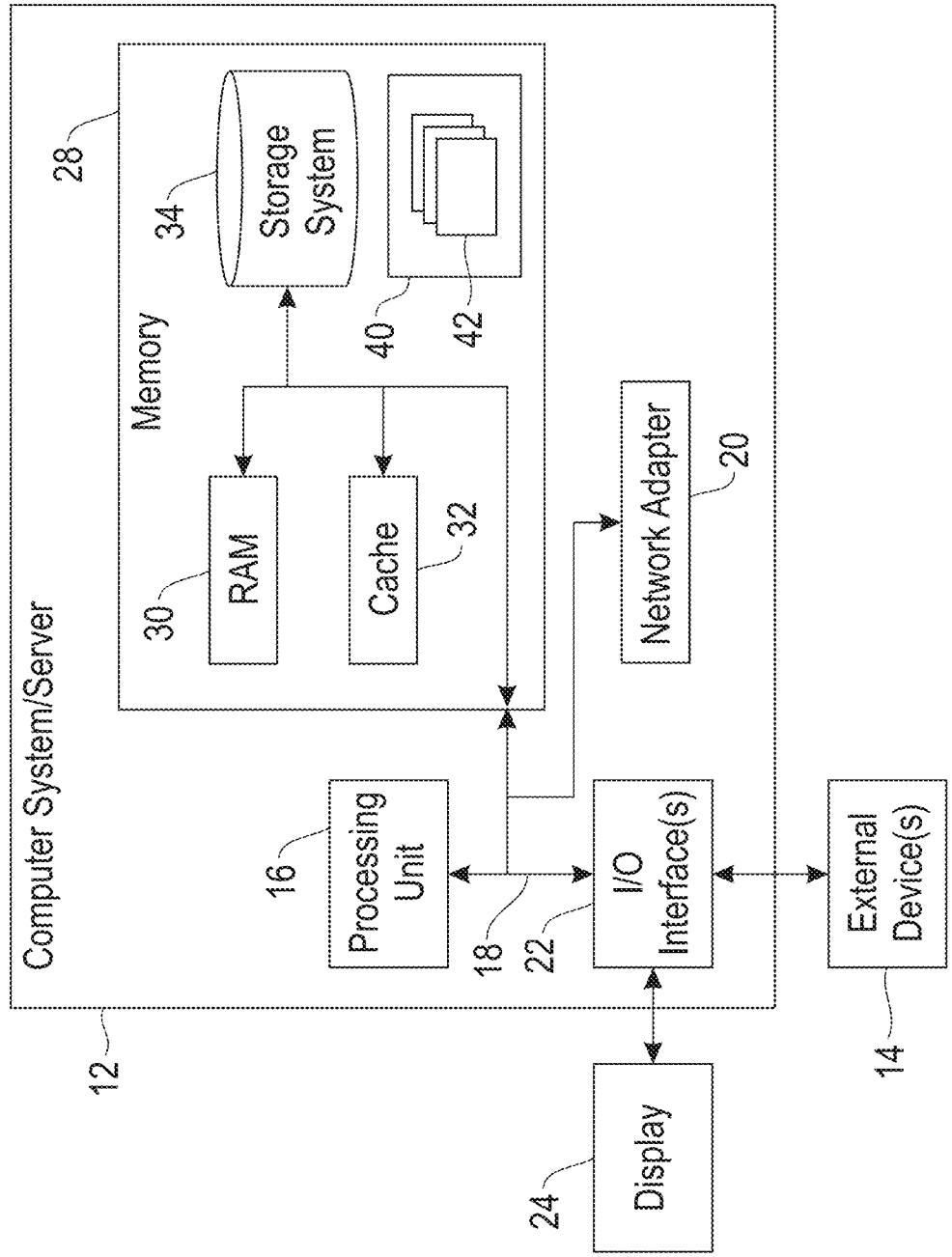
FIG. 12 depicts a computing node according to embodiments of the present disclosure.

Referring now to FIG. 12, a schematic of an example of a computing node is shown. Computing node 10 is only one example of a suitable computing node and is not intended to suggest any limitation as to the scope of use or functionality of embodiments of the disclosure described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 12, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the disclosure as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
receiving a candidate segmentation of a current medical image, the candidate segmentation representing an estimated boundary of an anatomical feature in the current medical image;
providing the candidate segmentation to a first trained classifier; and
receiving from the first trained classifier a first indication of accuracy of the candidate segmentation based on one or more feature of the candidate segmentation, the first indication of accuracy relating to at least one of comparison of the estimated boundary to edges in the medical image, a determination of smoothness of the estimated boundary, or a determination of continuity of the estimated boundary;
receiving one or more prior segmentation of a prior medical image of the anatomical feature, wherein said one or more prior segmentation does not include the candidate segmentation;
providing the candidate segmentation and said one or more prior segmentation to a second trained classifier;
receiving from the second trained classifier a second indication of accuracy of the candidate segmentation based on said one or more prior segmentation.

2. The method of claim 1, wherein the first indication of accuracy of the candidate segmentation comprises a probability.

3. The method of claim 1, wherein the first trained classifier comprises an artificial neural network.

4. The method of claim 1, wherein the second trained classifier comprises an artificial neural network.

5. The method of claim 1, further comprising: displaying to a user the candidate segmentation and said one or more prior segmentation;
prompting the user to adjust or approve the candidate segmentation.

6. The method of claim 1, further comprising:
displaying to a user the candidate segmentation;
prompting the user to adjust the candidate segmentation when the first indication of accuracy fails to meet a predetermined threshold.

7. The method of claim 1, wherein the candidate segmentation is automatically generated.

8. The method of claim 1, further comprising:
training the first trained classifier based on a plurality of automatically generated segmentations.

9. A system comprising:
a computing node comprising a computer readable storage medium having program instructions embodied therewith, the program instructions executable by a processor of the computing node to cause the processor to perform a method comprising:
receiving a candidate segmentation of a current medical image, the candidate segmentation representing an estimated boundary of an anatomical feature in the current medical image;
providing the candidate segmentation to a first trained classifier;
receiving from the first trained classifier a first indication of accuracy of the candidate segmentation based on one or more feature of the candidate segmentation, the first indication of accuracy relating to at least one of comparison of the estimated boundary to edges in the medical image, a determination of smoothness of the estimated boundary, or a determination of continuity of the estimated boundary;
receiving one or more prior segmentation of a prior medical image of the anatomical feature, wherein said one or more prior segmentation does not include the candidate segmentation;
providing the candidate segmentation and said one or more prior segmentation to a second trained classifier; and
receiving from the second trained classifier a second indication of accuracy of the candidate segmentation based on said one or more prior segmentation.

10. A computer program product for evaluation of segmentation of medical imagery, the computer program product comprising a computer readable storage medium having program instructions embodied therewith, the program instructions executable by a processor to cause the processor to perform a method comprising:
receiving a candidate segmentation of a current medical image, the candidate segmentation representing an estimated boundary of an anatomical feature in the current medical image;
providing the candidate segmentation to a first trained classifier;
receiving from the first trained classifier a first indication of accuracy of the candidate segmentation based on one or more feature of the candidate segmentation, the first indication of accuracy relating to at least one of comparison of the estimated boundary to edges in the medical image, a determination of smoothness of the estimated boundary, or a determination of continuity of the estimated boundary;
receiving one or more prior segmentation of a prior medical image of the anatomical feature, wherein said one or more prior segmentation does not include the candidate segmentation;
providing the candidate segmentation and said one or more prior segmentation to a second trained classifier;

receiving from the second trained classifier a second indication of accuracy of the candidate segmentation based on said one or more prior segmentation.

11. The computer program product of claim 10, wherein the first indication of accuracy of the candidate segmentation comprises a probability.

12. The computer program product of claim 10, wherein the first trained classifier comprises an artificial neural network.

13. The computer program product of claim 10, wherein the second trained classifier comprises an artificial neural network.

14. The computer program product of claim 10, the method further comprising:
   displaying to a user the candidate segmentation and said one or more prior segmentation;
   prompting the user to adjust or approve the candidate segmentation.

15. The computer program product of claim 10, the method further comprising:
   displaying to a user the candidate segmentation;
   prompting the user to adjust the candidate segmentation when the first indication of accuracy fails to meet a predetermined threshold.

16. The computer program product of claim 10, the method further comprising:
   training the first trained classifier based on a plurality of automatically generated segmentations.

\* \* \* \* \*